United States Patent [19]

Peters et al.

[11] Patent Number: 5,288,310
[45] Date of Patent: Feb. 22, 1994

[54] ADSORBENT TRAP FOR GAS CHROMATOGRAPHY

[75] Inventors: Anita J. Peters, Farmington Hills; Richard D. Sacks, Ann Arbor, both of Mich.

[73] Assignee: The Regents of the University of Michigan, Ann Arbor, Mich.

[21] Appl. No.: 953,893

[22] Filed: Sep. 30, 1992

[51] Int. Cl.⁵ .................................. B01D 15/08
[52] U.S. Cl. ................................ 96/104; 96/105
[58] Field of Search ................... 55/67, 197, 386

[56] References Cited

U.S. PATENT DOCUMENTS

| | | | |
|---|---|---|---|
| 2,757,541 | 8/1956 | Watson et al. | 73/422 |
| 2,920,478 | 1/1960 | Golay | 55/197 X |
| 2,972,246 | 2/1961 | Reinecke et al. | 73/23 |
| 2,981,092 | 4/1961 | Marks | 73/23 |
| 3,000,218 | 9/1961 | Marks et al. | 55/67 X |
| 3,111,835 | 11/1963 | Jenkins | 73/23 |
| 3,119,251 | 1/1964 | Bowers | 73/23 |
| 3,136,616 | 6/1964 | Thompson | 55/67 |
| 3,182,394 | 5/1965 | Jentzsch | 55/386 X |
| 3,201,922 | 8/1965 | Villalobos | 55/67 |
| 3,201,971 | 8/1965 | Villalobos | 73/23.1 |
| 3,220,164 | 11/1965 | Golay | 55/67 |
| 3,223,123 | 12/1965 | Young | 137/625.46 |
| 3,357,158 | 12/1967 | Hollis | 55/197 X |
| 3,386,279 | 6/1968 | Sternberg | 73/23.1 |
| 3,387,710 | 6/1968 | Pogacar | 55/197 X |
| 3,444,722 | 5/1969 | Roof | 73/23.1 |
| 3,477,207 | 11/1969 | Auger | 55/197 |
| 3,496,702 | 2/1970 | Carel et al. | 55/67 |
| 3,537,297 | 11/1970 | Loyd et al. | 73/23.1 |
| 3,550,428 | 12/1970 | Mator et al. | 73/23.1 |
| 3,628,872 | 12/1971 | Miranda | 356/201 |
| 3,630,371 | 12/1971 | Hrdina | 55/67 X |
| 3,663,263 | 5/1972 | Bodre et al. | 55/386 X |
| 3,676,649 | 7/1972 | Burk | 73/23.1 X |
| 3,728,845 | 4/1973 | Haruki et al. | 55/197 X |
| 3,735,565 | 5/1973 | Gilby et al. | 55/197 |
| 3,798,973 | 3/1974 | Estey | 73/23.1 X |
| 3,948,602 | 4/1976 | Solomon | 55/67 X |
| 4,035,168 | 7/1977 | Jennings | 55/67 |
| 4,038,053 | 7/1977 | Golay | 55/160 |
| 4,126,396 | 11/1978 | Hartmann et al. | 356/434 |
| 4,192,614 | 3/1980 | deMey, II et al. | 356/410 |
| 4,199,260 | 4/1980 | Kusnetz et al. | 356/411 |
| 4,204,952 | 5/1980 | Snyder | 55/67 X |
| 4,271,697 | 6/1981 | Mowery, Jr. | 73/61.1 C |
| 4,274,967 | 6/1981 | Snyder | 210/659 |
| 4,350,586 | 9/1982 | Conlon et al. | 55/197 X |
| 4,432,649 | 2/1984 | Krause | 356/438 |
| 4,447,266 | 10/1984 | Yang et al. | 55/67 |
| 4,468,124 | 8/1984 | Berick | 356/411 |
| 4,470,832 | 9/1984 | Sugawara et al. | 55/197 |
| 4,475,813 | 10/1984 | Munk | 356/73 |
| 4,536,199 | 8/1985 | Toon | 55/67 |
| 4,617,032 | 10/1986 | Wells | 55/67 |
| 4,805,441 | 2/1989 | Sides et al. | 55/67 X |
| 4,861,358 | 8/1989 | Mueller et al. | 55/386 |
| 4,863,871 | 9/1989 | Munari et al. | 436/161 |
| 4,923,486 | 5/1990 | Rubey | 55/197 X |
| 4,932,272 | 6/1990 | Hogg | 73/864.83 |
| 4,962,042 | 10/1990 | Morabito et al. | 436/161 |
| 5,028,243 | 7/1991 | Rubey | 55/67 |
| 5,096,471 | 3/1992 | Sacks et al. | 55/197 X |
| 5,141,532 | 8/1992 | Sacks et al. | 55/197 X |
| 5,141,534 | 8/1992 | Sacks et al. | 55/197 |

OTHER PUBLICATIONS

Scientific American by Walker-1986 pp. 118-124.
"Electrically Heated Cold Trap Inlet System for High--Speed Gas Chromatography"-Ewels et al.-1985, American Chemical Society.
"Evaluation of a Nitrogen-Cooled, Electrically Heated Cold Trap Inlet for High-Speed Gas Chromatography"-Mouradian et al.-1990, J. Chrom. Science, vol. 28.

(List continued on next page.)

Primary Examiner—Robert Spitzer
Attorney, Agent, or Firm—Harness, Dickey & Pierce

[57] ABSTRACT

A gas chromatography system in which prefocusing of a sample analyte is provided through the use of an adsorbent coated porous layer open tubular trap tube. Through the use of an adsorbent coated collection device low boiling point components can be successfully trapped for preconcentration and injection at temperatures well above that necessary when employing conventional cryo-focusing.

35 Claims, 3 Drawing Sheets

OTHER PUBLICATIONS

Fast-GC for Industrial Hygiene Analysis-Levine et al. 1985.

"Electrically Heated Cold Trap Inlet System for Computer-Controlled High-Speed Gas Chromatography'-'-Lanning et al.-1988, Anal. Chem., 60, 1994-1996.

"Large Volume Sample Introduction into Narrow Bore Gas Chromatography Columns using Thermal Desorption Modulation and Signal Averaging"-Liu et al.-1989.

"Liquid Chromatography Absorbance Detector With Retroreflective Array for Aberration Compensation and Double Pass Operation"-Pang et al.-1985, Am. Chem. Soc.

"Measurements of Organic Vapors at Sub-TLV Concentrations Using Fast Gas Chromatography'-Mouradian et al.-1990, Am. Ind. Hyg. Assoc., J. 51(2):90-95.

"Rapid Evaporation of Condensed Gas Chromatographic Fractions" Hopkins et al.-1978, J. of Chrom. 158, 465-469.

"Sample Enrichment in High Speed Narrow Bore Capillary Gas Chromatography"-Vanes et al.-1988, J. High Resolution, Chrom. & Chrom. Com., vol. 11, 852-857.

"Simultaneous Analysis of Methane and Non-Methane Hydrocarbons in Air Using Gas Chromatography/Frame Ionization Detection With a Solid Sorbent Sample Interference"-Zweidinger et al.-1990.

Theoretical Aspects and Practical Potentials of Rapid Gas Analysis in Capillary Gas Chromatography-Tijssen et al.-1987, Anal. Chem., 59, 1007-1015.

ADSORBENT TRAP FOR GAS CHROMATOGRAPHY

BACKGROUND AND SUMMARY OF THE INVENTION

This invention relates to a gas chromatography analysis instrument, and in particular, to a trap system for preconcentration and injection of a sample which employs an adsorbent coated trap column.

Gas chromatography is unsurpassed in its selectivity, sensitivity, and cost effectiveness. It is applicable for at least several hundred thousand compounds of low to moderate boiling point including compounds in the $C_1$ to $C_5$ range. The process is also unique in its ability to obtain complete speciation of complex mixtures of compounds.

In gas chromatography analysis the analyte mixture is separated into its components by eluting them from a column having a sorbent by means of a moving gas. In gas-liquid chromatography, which is the type most widely used at present, the column comprises a nonvolatile liquid sorbent coated as a thin layer on an inner support structure, generally the inside surface of a capillary tube. The moving gas phase, called the carrier gas, flows through the chromatography column. The analyte partitions itself between the moving gas phase and the sorbent and moves through the column at a rate dependent upon the partition coefficients or solubilities of the analyte components. The analyte is introduced at the entrance end of the column within the moving carrier gas stream. The components making up the analyte become separated along the column and elute at intervals characteristic of the properties of the analyte components. A detector, for example, a thermal conductivity detector or a flame ionization detector (FID) at the exit end of the analytical column responds to the presence of the analyte components. Upon combustion of the eluted components at the FID, charged species are formed in the flame. The flame characteristics are monitored through a biased ion detector which, along with associated signal processing equipment, produces a chromatogram which is a time versus detector signal output curve. The trace for complex mixtures includes numerous peaks of varying intensity. Since individual constituents of the analyte produce peaks at characteristic times and whose magnitude is a function of their concentration, much information is gained through an evaluation of a chromatogram.

Gas chromatography is often used for measuring the presence of minute concentrations of organic compounds. In order to permit an evaluation of a sample it generally must be enriched and introduced into the analytical column as a narrow sample "plug" so that the components eluting from the analytical column provide an adequate signal level with good output resolution.

Great strides have been made in the development of gas chromatography systems. The technique, however, provides additional opportunities for exploitation. One of the challenges posed to designers and users of gas chromatography equipment is a desire to provide fast analysis time needed, for example, to permit industrial process stream control or monitoring of internal combustion engine exhaust gases. In such applications, time dependent changes in concentrations of the analyte components can occur. Rapid analysis time permits analysis despite such transients.

In order to enrich organic compounds in vapor streams and inject them as a narrow sample plug to the separation column, electrically heated cold traps with bare metal tubes have been used extensively. The bare metal capillary tube is cooled to cryogenic temperatures and a sample analyte is admitted. The analyte materials undergo a phase change and adhere to the inside surface of the tube. After sample collection and enrichment, the metal tube is heated by passing an electric current through it. In a very short time, the tube is heated to a temperature sufficient to vaporize the trapped compounds. This results in a concentrated vapor plug which is injected into a gas chromatograph column. Such cold trapping or "cryo-focusing" can result in large concentration enrichments and very narrow injection bandwidths for the analysis of samples.

In some applications of gas chromatography analysis there is a desire to detect and measure concentrations of extremely low boiling point gases such as methane. While bare metal cold traps operate in a generally satisfactory manner, many lower boiling point compounds are difficult to cryo-focus in a bare metal tube because of the very low temperatures needed. In many applications, for example an industrial settings or where mobile monitoring may be desired, the availability of cryogenic temperatures is limited, and if necessary, poses a significant cost penalty and limits operational flexibility.

In accordance with the present invention, a gas chromatography apparatus is provided which enables rapid evaluation time and further enables the trapping and reinjection of very low boiling point gases including methane, which is notoriously difficult to trap. In accordance with this invention, a trap is provided in the form of a capillary tube which is coated with a substance which shows retention by adsorption of the compounds of interest For such adsorbent coated cold traps, efficient trapping and large concentration enrichments can be obtained at temperatures well above conventional trapping temperatures of the compounds. This can greatly reduce the cooling requirements for these devices. In accordance with this invention, several approaches toward implementing such an adsorbent coated trap are disclosed, including a system in which sample collection and reinjection occurs as the carrier gas stream flows through the trap in one direction, and an embodiment in which gas flow direction is reversed between operating modes. In addition to the adsorbent coated trap functioning as a means of concentration and reinjection of the analyte, the retention of the components of the mixture through adsorption on the column can be used as a means of initial separation of the analyte components.

Additional benefits and advantages of the present invention will become apparent to those skilled in the art to which this invention relates from the subsequent description of the preferred embodiments and the appended claims, taken in conjunction with the accompanying drawings.

DETAILED DESCRIPTION OF THE INVENTION

Figure 1:
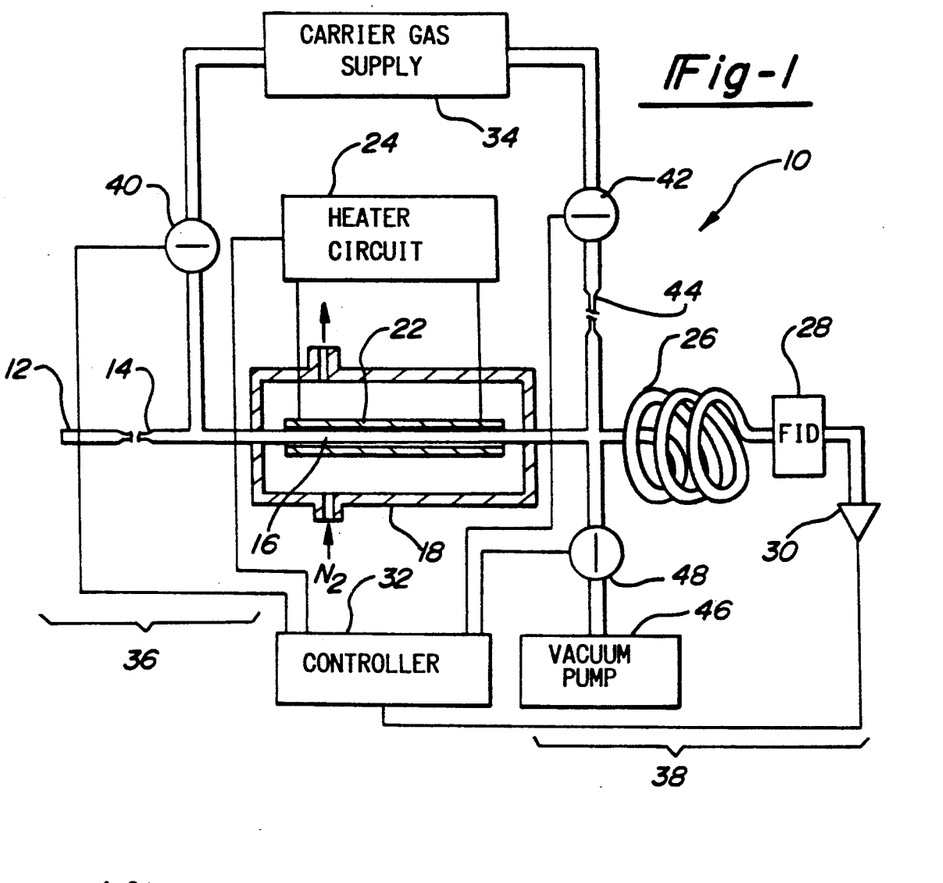
FIG. 1 is a schematic diagram of a gas chromatography system in accordance with a first embodiment of the invention.

A gas chromatography system in accordance with a first embodiment of this invention is shown in FIG. 1 and is generally designated there by reference number 10. Sample inlet 12 receives a sample to be evaluated which may be an atmospheric air sample or some other analyte. The sample flows from inlet 12 through pneumatic restrictor 14 which is a length of deactivated fused silica glass capillary tube provided for the purpose of controlling gas flow rates. Sample inlet 12 and restrictor 14 together comprise an inlet branch 36 of system 10.

Restrictor 14 is connected to trap tube 16 enclosed within cooling chamber 18. In accordance with this invention, trap tube 16 is of capillary dimension and includes an adsorbent coating on its inner surface. Trap tube 16 is classified as a porous layer open tubular (PLOT) configuration. Various types of stationary phase adsorbent materials can be used. In connection with this invention one material investigated was $Al_2O_3$ and other a commercially available PLOT column known as PoraPLOT Q having an adsorbent coating of styrene-divinylbenzene. The $Al_2O_3$ column investigated had an inside diameter of 0.32 mm with a 15 cm length and the stationary phase material had a coating thickness of 5 micrometers. The $Al_2O_3$ material has a maximum operating temperature of 250° C. and is best employed in trapping hydrocarbons in the $C_1$-$C_{10}$ range. The PoraPLOT Q column investigated also had an inside diameter of 0.32 mm and a 15 cm length. The PoraPLOT Q stationary phase material has a film thickness of 10 micrometers, with a maximum temperature of 200° C. Applications for the PoraPLOT Q material include alcohols, water, polar volatiles, and various hydrocarbons and gases. Gas chromatography system 10 is designed for high speed operation and, therefore, short column lengths are used and an attempt is made to minimize system "dead volume". In view of these considerations, it is believed that the length of trap tube 16 should not exceed 50 cm, and its inside diameter should be less than 1 mm and preferably around 0.5 mm.

Cooling chamber 18 can be formed from quartz and includes features for controlling the temperature of trap tube 16. In the embodiment shown, chamber 18 is cooled using a source of cold gas such as $N_2$ gas which provides a trapping temperature. Trap tube 16 also must be heated for the desorption of trapped materials. One approach toward providing such heating is to place trap tube 16 within closely fitting metal tube 22 which can be resistively heated. Heater circuit 24 which may be provided in the form of a capacitive discharge heater circuit as described in U.S. Pat. No. 5,096,471, which is hereby incorporated by reference, is provided to generate a resistance heating pulse for metal tube 22 which when heated, heats trap tube 16 for causing desorption. Because of the high thermal compliance of the thin-walled fused silica adsorbent coated trap tube 16, it heats rapidly in response to heating of metal tube 22.

After desorption, the analyte is driven by the flow of a carrier gas to outlet branch 38 where it passes into analytical separation column 26 which may take various forms including another PLOT type column or a more conventional type having a liquid stationary phase Materials which elute from separation column 26 pass into a detector which is shown in the form of a flame ionization detector (FID) 28. An electrometer 30 is used to quantify the output of FID 28 based on the existence of charged species which are produced upon elution of components of the analyte mixture. Controller 32 receives an input from electrometer 30 and through an appropriate interface provides a chromatogram trace. Controller 32 also controls operation of the system including the injection sequence and gas flow management, as will be described in more detail.

A supply 34 of a carrier gas such as helium or hydrogen is provided which is connected to both inlet branch 36 and outlet branch 38 through valves 40 and 42, respectively. Pneumatic restrictor 44 is provided between valve 42 and its connection with outlet branch 38 for the purpose of fluid flow rate control. Vacuum pump 46 also is connected into outlet branch 38 through valve 48.

During sample collection, valves 40 and 42 are closed and valve 48 is open. This isolates the system from carrier gas supply 34 and connects the inlet branch 36 to vacuum pump 46. As long as the vacuum pump pressure is less than that at sample inlet 12, the sample will be drawn into trap tube 16 which, in the collection mode, is maintained at a cold collection temperature. During the sample collection interval, vacuum pump 46 also causes separation column 26 to be backflushed and the FID 28 gases rapidly purge the column of any high boiling point residues from a previous sample. After sample collection the system transitions to the injection mode in which valve 42 remains closed, but valve 40 is open and valve 48 is closed. Trap tube 16 is then heated by heater circuit 24 to inject the sample into analytical column 26. In some applications, the heating of trap tube 16 would occur rapidly to minimize desorption time of all the trapped components depending on the degree of initial separation which occurs in trap tube 16 the desorbed components of the analyte may appear together as a single sample "plug" or may elute separately. In either case, however, the injection bandwidth of a particular component of the analyte needs to be minimized as a means of providing good resolution after a short separation time. For fast separation, the bandwidth of a particular desorbed component of the injected sample should be less than about 100 ms. After injection is complete, valve 42 is opened and valve 40 is closed. Carrier gas continues to drive the analyte through column 26 whereas trap tube 16 is being backflushed. Trap tube 16 is maintained at an elevated temperature during this interval to remove any residues from the trap tube. After elution is complete, analytical column 26 can be backflushed by opening valve 48, causing a reverse flow through the column.

Figure 2:
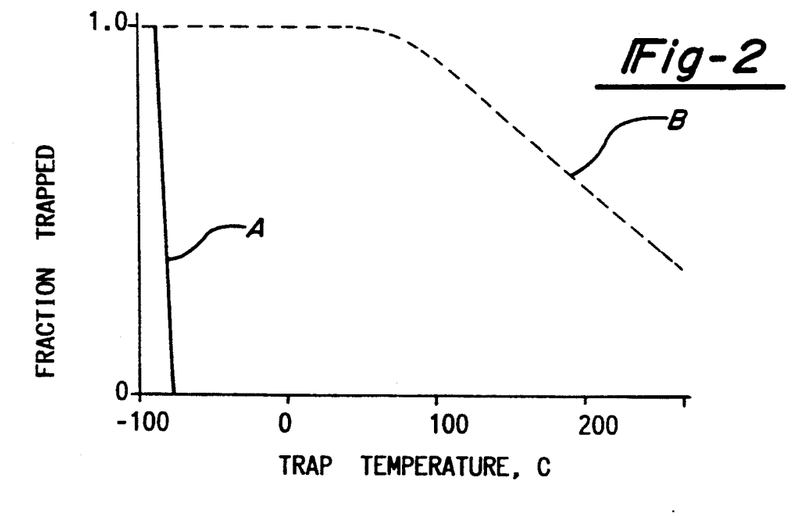
FIG. 2 is a plot of trapping ratio versus temperature for uncoated and adsorbent coated trap tubes.

FIG. 2 illustrates the fundamental differences in the behavior of adsorbent coated traps used in accordance with this invention as compared with uncoated traps. FIG. 2 plots the fraction of a single compound trapped vs. trap temperature and is based on empirical data for pentane. Curve A is a bare metal trap tube with an inside diameter of 0.30 mm. Curve B was obtained with a 0.32 mm inside diameter porous-polymer coated PLOT trap tube 16 contained within a close-fitting stainless steel tube 22. Two important differences are seen between the two plots. First, much lower temperatures are needed to obtain efficient collection of pentane with the bare metal tube (curve A). Second, the process is much more abrupt with the bare metal tube. For the bare metal tube, the fraction trapped goes from 0 to 1.0 over a temperature range of only a few degrees; while for the PLOT trap tube (curve B), a temperature change of over 200° C. is inadequate to obtain the same result. In fact, the PLOT trap shows considerable sample collection at temperatures of 250° C. which is near the maximum operating temperature for the trap tube material. In addition, even at very low temperatures, the fraction trapped is slightly less than 1.0. Trapping in a bare metal tube is a physical process consisting of a phase change referred to as cyro-focusing the sample. Trapping on an adsorbent stationary phase trap is a chemical process which may be referenced to as chemi-focusing. For the bare metal trap tube (curve A), if the temperature is less than about −80° C., the entire sample is trapped. If the temperature is then increased to about −70° C., the entire sample is released. For the PLOT trap (curve B), nearly complete sample collection occurs at very low temperature, and a more gradual release of the sample occurs when the trap is heated.

In defining the operating parameter and behaviors of PLOT column trap tube 16, several definitions and characteristics are of importance. The sample capacity factor k is defined as the ratio of the amount of a particular sample species sorbed on the solid surface of trap tube 16 to the amount in the gas phase. The amount of sample that can be sorbed under a specified set of conditions on trap tube 16 is defined as the absolute capacity C. From the definition of k, the fraction trapped in curve B of FIG. 2 is given by $k/(k+1)$. Three important aspects of the PLOT trap 16 operation are the injection time or delay time t, the injection bandwidth s, and the preconcentration factor A. The transport time of carrier gas through trap 16 $t_g$ is given by the ratio of trap length L to gas velocity v. A typical length of trap tube 16 is about 10 cm, and the velocity of carrier gas from source 34 is usually in the range from 100 to 1000 cm/s. Thus, $t_g$ is in the range from 10 to 100 ms. Because of the short length of trap tube 16, gas compression effects are minimal, and the gas flow velocity can be assumed constant along the length of the trap.

For a bare metal trap tube, the value of C is limited only by the amount of sample that will physically block the tube and choke off sample gas flow. Also, for the bare metal trap, the sample injection delay after the tube is heated is just $t_g$ or less, and the injection bandwidth s is typically about 10 ms. If the value of k for PLOT trap tube 16 is very large during sample collection and if the trap capacity C is not exceeded, it can be assumed that the collected sample plug migrates only a relatively short distance along the tube during the sample collection interval. Under these conditions, the injection delay is given by $t_g(k_d+1)$, where $k_d$ is the capacity factor for the sample component of interest during the desorption heating cycle. The preconcentration factor is nearly proportional to $(k_c+1)/(k_d+1)$, where $k_c$ is the sample capacity factor during sample collection. The injection bandwidth is nearly proportional to $k_d+1$.

For operation as an inlet system for high-speed gas chromatography, trap tube 16 is cooled to a sufficiently low temperature to obtain minimum sample plug migration during the sample collection interval and to obtain the largest possible preconcentration factor $k_c$. To inject the sample, trap tube 16 is rapidly heated to the injection or desorption temperature, and this temperature is maintained until all components of interest have migrated through the trap tube and entered separation column 26. Note that both the $k_c$ and $k_d$ values are very temperature dependent and are different for every sample compound. As long as the migration rate in trap tube 16 is low during sample collection, breakthrough (i.e. elution during sample collection) should not occur and peak areas in the final chromatograms should be independent of the $k_c$ value. Injection bandwidth for a particular compound, however, should vary somewhat with the $k_c$ value.

Due to the retention characteristics of trap tube 16, during the desorption mode individual components of the analyte may desorb at different times. This retention characteristic can be exported to enable multi-dimensional separation in which trap tube 16 functions both as a collection device and provides initial separation. This initial separation allows selective introduction of sample components to analytical column 26. In systems utilizing trap tube 16 in this manner a longer duration and a more controllable heating pulse may be required than can be delivered using capacitive-discharge heater circuit 24. Even when the total desorption time is many seconds in duration, trap tube 16 would deliver individual components over a short injection bandwidth of less than 100 ms.

In gas chromatography system 10, separation column 26 can also be a PLOT configuration column which shows significant retention of the target compounds at the anticipated injection (desorption) temperatures. In fact, separation column 26 can be a segment of a continuous capillary tube, a portion of which is enclosed by cooling chamber 18.

Figure 3A:
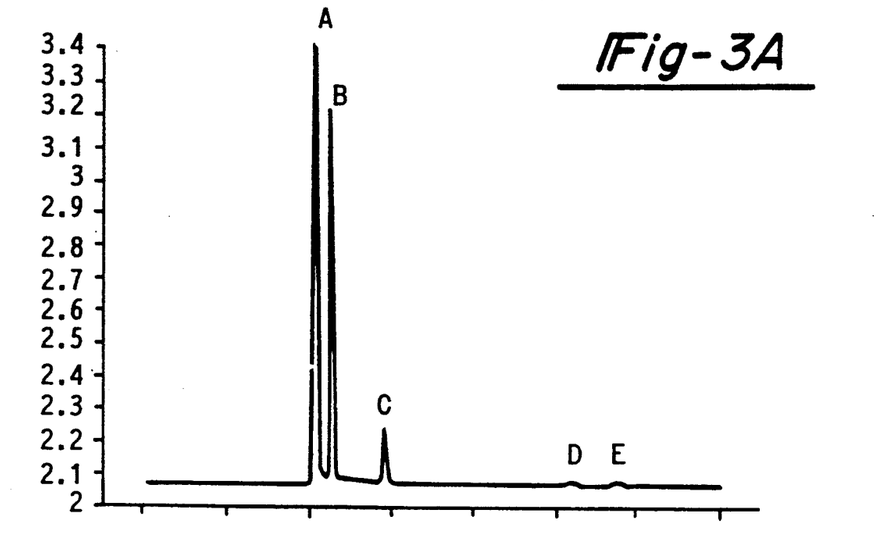
FIG. 3 is a series of chromatograms labeled 3a, 3b, and 3c representing various trapping temperatures for a gas chromatography system according to the invention.
Figure 3B:
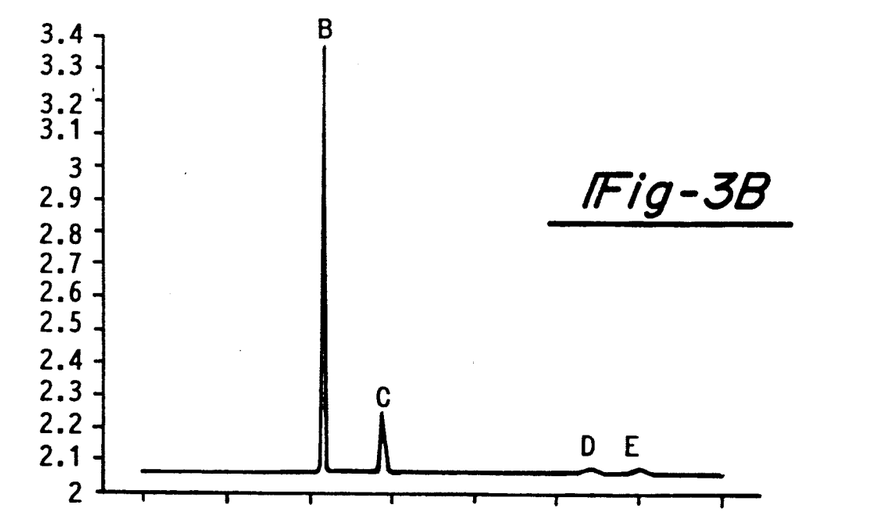
Figure 3C:
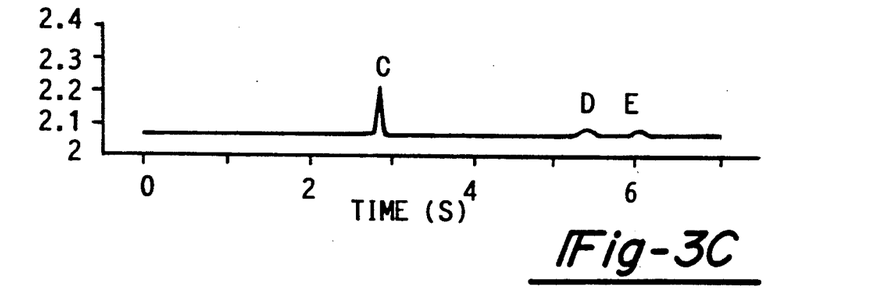

As a representative example of a system in accordance with the invention, FIG. 3 shows high-speed chromatograms of a natural gas sample obtained using a 15-cm long, 0.32-mm i.d. PoraPLOT Q trap tube 16 and a 4.0-meter long, 0.32-mm i.d. $Al_2O_3$ PLOT analytical separation column 26. Chromatograms 3a, 3b and 3c correspond to trapping temperatures of −130° C., −70° C. and −30° C., respectively. Each of the chromatograms were obtained with an injection temperature of 100° C. Components labeled A, B, C, D and E in FIG. 3 are both methane, ethane, propane, isobutane and normal butane, respectively. Note that very narrow peaks are produced because of the efficient sample trapping and the rapid heating of the trap tube. Separation is complete in about 6 seconds. At the lowest trapping temperature shown in FIG. 3a, all components are collected in the trap including methane, which is notoriously difficult to trap. At the intermediate temperature shown in FIG. 3b, methane is not significantly collected (no methane peak is observed) but all other components are quantitatively collected. At the highest temperature shown in FIG. 3c, neither methane nor ethane are significantly retained in the cold trap but all other components are quantitatively collected.

In the gas chromatography system according to this invention, a number of parameters and operating characteristics must be selected depending upon the type of analyte and separation desired. The selection of adsorbent material has the significant impact on the trap operation. For example, the PoraPLOT Q trap investigated by the inventors exhibited stronger retention of components at a given temperature as compared with an $Al_2O_3$ coated column. This difference is, perhaps attributed to the fact that the primary mode of collection of the $Al_2O_3$ column is through adsorption whereas a PoraPLOT Q column traps components through a combination of diffusion and adsorption. As illustrated in FIG. 3 trapping temperature must be selected to provide the degree of sample enrichment desired. The fraction adsorbed for both types of traps increases with decreasing trap temperature. The reinjection or desorption temperature must also be selected carefully. At higher reinjection temperatures components will be less retained and the peaks of the output will, therefore, be less broadened. The absolute capacity of the column must also be considered so as not to exceed the trap capacity which would result in sample bleed-off. The firing delay or sample collection interval must be selected so that an acceptable degree of sample enrichment occurs while avoiding bleed-off which occurs in an adsorbent column, since even when the analyte components are adsorbed they constantly move along the column in the direction of the flow of carrier gas.

Preliminary quantitative studies have shown that linear calibration curves of peak area vs. mass of the trapped sample can be obtained using the adsorbent-coated cold trap inlet system of this invention. An $Al_2O_3$ trap tube 16 gave correlation coefficients in the range 0.9986 to 0.9993 for samples in the range from 1.0 ng to 30 ng.

A known concern when using some PLOT columns or other adsorbent columns is their affinity for polar molecules such as water. Excess concentrations of water adsorbed onto the column can foul the column and be troublesome to remove. In order to eliminate this effect, one approach is to prevent water vapor from coming into contact with the adsorption column. Another approach toward reducing the problems of fouling of an adsorbent trap is to cause the sample to be trapped at the end of the trap tube 16 closest to analytical column 26. This is achieved by directing carrier gas flow through the trap tube in opposite direction in the trapping and reinjection modes. Through such gas flow management, the sample is not required to traverse the entire length of the trap tube which increases fouling problems. Such a system using a bare metal trap tube is described in U.S. Pat. No. 5,141,532, which is hereby incorporated by reference.

Figure 4:
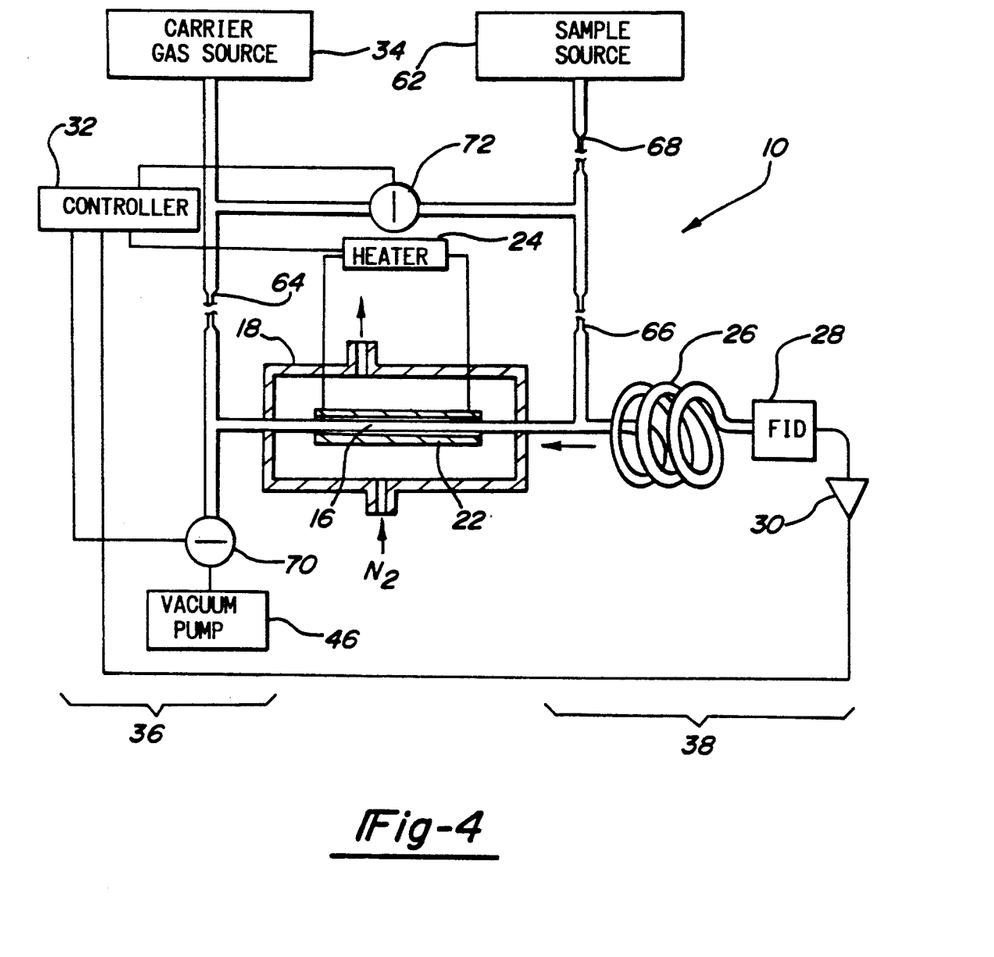
FIG. 4 is a schematic diagram of a gas chromatography system in accordance with a second embodiment of this invention.

FIG. 4 provides an illustration of a "reverse flow" system using an adsorbent trap tube and is generally designated by reference number 60. Since many elements of system 60 are identical to those of system 10, common reference numbers for such elements are used. As shown, gas chromatography system 60 includes cooling chamber 18 having inlets and outlets for conducting the flow of a cryogenic gas such as nitrogen. Trap tube 16 passes through chamber 18 and conducts the analyte through the chamber. Trap tube 16, as in the first embodiment, is of a PLOT column configuration. Heater circuit 24 is connected to metal tube 22 as in the prior embodiment. Trap tube 16 is connected to analytical separation column 26. The opposite end of column 26 is connected to FID 28. Carrier gas source 34 provides the source of a carrier gas such as hydrogen or helium and communicates with trap tube 16 through a first conduit branch 74 comprising the elements to the left of trap tube 16 as shown in FIG. 4. Sample source 62 provides a sample at a pressure which is less than that of carrier gas source 34 and may be at ambient pressure or below and is connected between trap tube 16 and column 26 to a second conduit branch 76 comprising the elements to the right of trap tube 16. Vacuum pump 46 communicates through first branch 74 with one end of trap tube 16. As shown, various pneumatic restrictors 64, 66 and 68 are provided which are comprised of varying lengths of capillary tube which are used to control the flow rates of fluids through the various flow paths.

A pair of valves 70 and 72 are provided which are preferably pneumatically or electrically controlled on-/off valves. As shown, valve 72 controls the flow of fluid between first and second branches 74 and 76, and valve 70 selectively exposes one end of trap tube 16 to vacuum pump 46. Operation of valves 70 and 72, heater circuit 24 and vacuum pump 46 is coordinated by controller 32.

In operation of system 60, when it is desired to trap a sample, valve 70 is opened and valve 72 is closed. By having valve 70 opened, vacuum pump 46 serves as the lowest pressure point for the three separate flow paths originating at carrier gas source 34, sample source 62, and detector 28. Thus, fluids flow through all of the flow paths toward vacuum pump 46. In this mode, cooling chamber 18 is at a low temperature and, therefore, the sample is being introduced into trap tube 16 at its end closest to analytical column 26 (i.e. flow is right-to-left). A small amount of carrier gas is continually vented through vacuum pump 46.

After a sample collection interval of, for example, several seconds, valve 72 is opened and valve 70 is closed which corresponds to an injection mode of operation. Simultaneously, a heating pulse is provided by heater circuit 24 to desorb the collected sample. In this mode, detector 28 which is exposed to atmospheric pressure constitutes the lowest pressure point of the system. A primary flow of carrier gas in this desorption mode is through restrictor 64 and then into trap tube 16 through its end furthest from column 26 (i.e. flow is left-to-right) and into column 26. A secondary flow of carrier gas originates from source 34, travels through valve 72, restrictor 66 and then to column 26 and thus clears portions of second branch 76. The relative flow rate through these two paths are determined by the characteristics of restrictors 64 and 66. It is also significant that during the injection a desorption mode of operation, a reverse flow occurs through restrictor 68 which has the effect of purging the conduit and that restrictor, thus eliminating the remanents of prior samples from influencing subsequent evaluation. It should be further noted that the flow of carrier gas through restrictor 66 dilutes the sample being introduced injected into column 26. Accordingly, it is important to limit the flow rate through this pathway. As mentioned previously, during the injection mode, the sample which has collected at the end of trap tube 16 closest to column 46 is directly inputed into the column without passing through the remainder of the trap tube.

In a backflush mode of operation of gas chromatography system 60, both valves 70 and 72 are opened and heating of trap tube 16 continues. In this mode, both carrier gas source 34 and detector 28 serve as high pressure points for the system, whereas vacuum pump 46 defines the low pressure point. Any analyte components remaining in column 26 will be redirected back into trap tube 16 where they can be vented to vacuum pump 46. Since valve 72 is opened there remains a purge flow from carrier gas source 34 to sample source 62. Therefore, the system is not subject to contamination from the sample inlet during backflushing.

While the above description constitutes the preferred embodiments of the present invention, it will be appreciated that the invention is susceptible of modification, variation and change without departing from the proper scope and fair meaning of the accompanying claims.

We claim:

1. A gas chromatography system for the separation of components of a sample mixture, comprising:
   a trap in the form of a porous layer open tubular column having an adsorbent coating on the inside surface of said tube,
   temperature control means for causing said trap to be selectively held at a trapping temperature above the freezing point of a number of said components or a higher desorption temperature;
   fluid circuit means for causing the sample mixture to be introduced into said trap while said trap is at said trapping temperature causing at least some of the components of the sample mixture to be adsorbed onto said adsorbent coating and for causing said adsorbed components to be desorbed from said trap when said trap is at said desorption temperature, said desorbed components of the sample mixture being at least partially eluted, and
   a detector for receiving said desorbed component of the sample mixture and providing an output related to the concentrations of said desorbed components of the sample mixture.

2. A gas chromatography system according to claim 1 further comprising an analytical column connected to said trap for separation of the desorbed components of the sample mixture.

3. A gas chromatography system according to claim 2 wherein said analytical column has an adsorbent stationary phase.

4. A gas chromatography system according to claim 1 wherein the sample mixture includes hydrocarbons in the $C_1$ to $C_{10}$ range.

5. A gas chromatography system according to claim 1 wherein said temperature control means provides said trapping temperature by exposing said trap to a cold gas and said desorption temperature by a resistive heating element.

6. A gas chromatography system according to claim 1 wherein the sample mixture includes methane gas and the methane gas becomes adsorbed onto said trap when said trap is at said trapping temperature.

7. A gas chromatography system according to claim 1 wherein said trap is a porous layer open tubular column having said adsorbent coating of $Al_2O_3$.

8. A gas chromatography system according to claim 1 wherein said trap is a porous layer open tubular column having said adsorbent coating of Styrene-Divinylbenzene material.

9. A gas chromatography system according to claim 1 wherein said fluid circuit means causes the sample mixture to be trapped as a carrier gas flows through said trap in one direction and said flow continues in said one direction as said adsorbed components are desorbed.

10. A gas chromatography system according to claim 1 wherein said fluid circuit means causes the sample mixture to be trapped as a carrier gas flows through said trap in one direction as the components are adsorbed and said flow occurs in an opposite direction as said components are desorbed.

11. A gas chromatography system according to claim 1 wherein said trap tubular column has an inside diameter less than 1 mm.

12. A gas chromatography system according to claim 1 wherein said trap tubular column has a length less than 50 cm.

13. A gas chromatography system according to claim 1 wherein desorption of said adsorbed sample components occurs within an interval of less than 100 ms.

14. A gas chromatography system according to claim 1 wherein individual components of the sample mixture are desorbed from said trap tube at distinct time intervals and thus the components of the sample mixture are at least partially separated by said trap tubular column.

15. A gas chromatography system for the separation of components of a sample mixture, comprising:
   a trap in the form of a porous layer open tubular column having an adsorbent coating on the inside surface of said tube and said tube having an internal diameter less than 1 mm and a length of less than 50 cm,
   temperature control means for causing said trap to be selectively held at a trapping temperature above the freezing point of a number of said components or a higher desorption temperature,
   fluid circuit means for causing the sample mixture to be introduced into said trap while said trap is at said trapping temperature causing at least some of the components of the sample mixture to be adsorbed onto said adsorbent coating and for causing the adsorbed components to be desorbed from said trap when said trap is at said desorption temperature, said desorbed components of the sample mixture being at least partially eluted, said trap and said temperature control means causing the desorption of any of said adsorbed components of the sample mixture to be complete in less than 100 ms, and
   a detector for receiving said desorbed component of the sample mixture and providing an output related to the concentrations of said desorbed components of the sample mixture.

16. A gas chromatography system according to claim 15 further comprising an analytical column connected to said trap for separation of the components desorbed from said trap.

17. A gas chromatography system according to claim 16 wherein said analytical column has an adsorbent stationary phase.

18. A gas chromatography system according to claim 15 wherein the sample mixture includes hydrocarbons in the $C_1$ to $C_{10}$ range.

19. A gas chromatography system according to claim 15 wherein said temperature control means provides said trapping temperature by exposing said trap to a cold gas and said desorption temperature by a resistive heating element.

20. A gas chromatography system according to claim 15 wherein the sample mixture includes methane gas and the methane gas becomes adsorbed onto said trap when said trap is at said trapping temperature.

21. A gas chromatography system according to claim 15 wherein said adsorbent coating of $Al_2O_3$.

22. A gas chromatography system according to claim 15 wherein said adsorbent coating of Styrene-Divinylbenzene material.

23. A gas chromatography system according to claim 15 wherein said fluid circuit means causes the sample mixture to be trapped as a carrier gas flows through said trap in one direction and said flow continues in said one direction as said adsorbed components are desorbed.

24. A gas chromatography system according to claim 15 wherein said fluid circuit means causes the sample mixture to be trapped as a carrier gas flows through said trap in one direction as the components are adsorbed and said flow occurs in an opposite direction as said components are desorbed.

25. A gas chromatography system according to claim 24 wherein said desorption of any of said adsorbed sample component occurs within an interval of less than 100 ms.

26. A gas chromatography system according to claim 15 wherein individual components of the sample mixture are desorbed from said trap tube at distinct time intervals and thus the components of the sample mixture are at least partially separated by said trap tube.

27. A gas chromatography system for the separation of components of a sample mixture, comprising:
- a trap in the form of a porous layer open tubular column having an adsorbent coating on the inside surface of said tube,
- an analytical separation column connected to said trap,
- temperature control means for causing said trap to be selectively held at a trapping temperature above the freezing point of a number of said components or a higher desorption temperature,
- fluid circuit means for causing the sample mixture to be introduced into said trap while said trap is at said trapping temperature causing at least some of the components of the sample mixture to be adsorbed onto said adsorbent coating and for causing said adsorbed components to be desorbed from said trap when said trap is at said desorption temperature, said desorbed components of the sample mixture being at least partially eluted, and
- said fluid circuit means for causing said sample mixture to be introduced into said trap in a flow direction into an end of said trap connected to said analytical separation column, and in an opposite flow direction out of said end as said components are desorbed, and
- a detector for receiving said component after said desorption and providing an output related to the concentrations of said components in the sample mixture.

28. A gas chromatography system according to claim 27 wherein said analytical column has an adsorbent stationary phase coating.

29. A gas chromatography system according to claim 27 wherein the sample mixture includes hydrocarbons in the $C_1$ to $C_{10}$ range.

30. A gas chromatography system according to claim 27 wherein said temperature control means provides said trapping temperature by exposing said trap to cold gas and said desorption temperature by a resistive heating element.

31. A gas chromatography system according to claim 27 wherein the sample mixture includes methane gas and the methane gas comes adsorbed onto said trap when said trap is at said trapping temperature.

32. A gas chromatography system according to claim 27 wherein said adsorbent coating of $Al_2O_3$.

33. A gas chromatography system according to claim 27 wherein said adsorbent coating of Styrene-Divinylbenzene material.

34. A gas chromatography system according to claim 27 wherein said trap tubular column has an inside diameter less than 1 mm.

35. A gas chromatography system according to claim 27 wherein said trap tubular column has a length less than 50 cm.

* * * * *

UNITED STATES PATENT AND TRADEMARK OFFICE
CERTIFICATE OF CORRECTION

PATENT NO. : 5,288,310
DATED : February 22, 1994
INVENTOR(S) : Anita J. Peters, Richard D. Sacks It is certified that error appears in the above-indentified patent and that said Letters Patent is hereby corrected as shown below:

Column 12, line 22, Claim 31, after "gas" delete "comes" and insert --becomes--.

Column 12, line 26, Claim 33, delete "Agas" and insert therefor --A gas--.

Signed and Sealed this

Second Day of August, 1994

Attest:

BRUCE LEHMAN

*Attesting Officer*     *Commissioner of Patents and Trademarks*